United States Patent
Manmaru et al.

[11] Patent Number: 5,633,460
[45] Date of Patent: May 27, 1997

[54] OCEAN ENVIRONMENT MONITORING SYSTEM AND METHOD FOR CONTROLLING THE SAME

[75] Inventors: Kyoko Manmaru; Tsugio Shimono, both of Tokyo, Japan

[73] Assignee: NEC Corporation, Tokyo, Japan

[21] Appl. No.: 501,807

[22] Filed: Jul. 13, 1995

[30] Foreign Application Priority Data

| Jul. 14, 1994 | [JP] | Japan | 6-162241 |
| Dec. 15, 1994 | [JP] | Japan | 6-311690 |
| Jan. 17, 1995 | [JP] | Japan | 7-004863 |

[51] Int. Cl.⁶ .................................................. G01D 21/00
[52] U.S. Cl. .................................. 73/170.31; 73/178.29
[58] Field of Search .......................... 73/864.34, 863.83, 73/170.29, 170.31, 170.28

[56] References Cited

U.S. PATENT DOCUMENTS

| 3,241,512 | 3/1966 | Green | 114/222 |
| 3,824,852 | 7/1974 | Otto | 73/170.29 |
| 4,092,858 | 6/1978 | Edgerton | 73/170.29 |
| 4,256,556 | 3/1981 | Bennett et al. | 204/147 |
| 4,345,981 | 8/1982 | Bennett et al. | 204/129 |
| 4,384,943 | 5/1983 | Stoner et al. | 204/149 |
| 4,479,864 | 10/1984 | Kanai et al. | 204/290 F |

FOREIGN PATENT DOCUMENTS

| 58-103345 | 7/1983 | Japan . |
| 3-125690 | 5/1991 | Japan . |
| 4-148313 | 5/1992 | Japan . |

*Primary Examiner*—George M. Dombroske
*Assistant Examiner*—Ronald Biegel
*Attorney, Agent, or Firm*—Foley & Lardner

[57] ABSTRACT

An ocean environment monitoring system has a sensor inside a sensor chamber provided with a pair of electrodes at the inlet port of the chamber and a pump for introducing seawater inside the chamber. When a voyage is applied to the electrodes, seawater is electrolyzed to produce an antifouling substance. By operating the pump and a power supply unit for the electrodes intermittently, the antifouling substance is supplied to the filter, the interior of the sensor chamber and the sensor. The monitoring system is compact, consumes a reduced amount of electric power, performs measurement substantially without producing errors for a prolonged period of time, and effectively prevents settlement of marine organisms onto the sensor.

22 Claims, 7 Drawing Sheets

OCEAN ENVIRONMENT MONITORING SYSTEM AND METHOD FOR CONTROLLING THE SAME

BACKGROUND OF THE INVENTION (a) Field of the Invention:

The present invention relates to an ocean environment monitoring system and a method for controlling the same. More specifically, the present invention relates to a technique for preventing settlement of marine organisms on sensors used in an ocean environment monitoring system.

(b) Description of the Related Art:

After sensors for monitoring ocean environmental factors such as an electric conductivity of seawater, dissolved oxygen, etc., are located in seawater for a prolonged period of time, errors in measurements are generated due to dirt formed by the settlement of marine organisms (marine biofouling or biofouling). To prevent marine organisms from adhering or settling onto sensors disposed in direct contact with seawater, a method has been proposed in which the sensors are received in a chamber having an inlet port and an outlet port for seawater. The interior of the chamber and filters attached to the ports are made from a material producing copper ions therefrom.

A technique is known in which a direct current is supplied in an equipment of an on-shore plant which uses seawater or a structure or vessel used in oceans. The current flows through the seawater to electrolyze the seawater to produce an antifouling substance such as chlorine and hypochlorous acid, thereby preventing marine biofouling. Unlike copper ions, such an antifouling substance does not accumulate in the sea because it is decomposed by other substances in seawater, sunlight, and the like.

Examples of the method for preventing settlement of marine organisms onto the above structures utilizing electrolysis of seawater are described in Patent Publication Nos. JP-A-3-125690, JP-A-4-148313 and JP-B-58(1983)-103345. In the method described in JP-A-3-125690, current is supplied to flow through a conductive coating film coating an object to be protected, thereby producing an antifouling substance at the surface of the object. In the method described in JP-A-4-148313, seawater is electrolyzed in an electrolysis vessel to produce an antifouling substance, the antifouling substance being included in seawater passing in the vicinity of an object to be protected.

In preventing settlement of marine organisms onto sensors used for monitoring an ocean environment, it is desired that such protection of the sensors can be made at a low cost without causing environmental contamination and that the monitoring system including such a protection can be easily maintained. However, the conventional method for producing copper ions in the sensor chamber only provides insufficient effects, and filters disposed at the inlet port and outlet port for seawater must be exchanged at least each month or every two months because these filters become clogged by settlement of marine organisms and the like. In addition, since copper ions, which are not considered entirely harmless, are continuously dissolved into seawater, a risk in environmental contamination exists.

The method in which marine biofouling is prevented by using an antifouling substance, which is produced by electrolysis of seawater by using direct current, has been applied to some structures used in oceans. However, the method has never been applied to sensors used in an ocean environment monitoring system. If the method, in which an antifouling substance is produced on the surface of an object to be protected, is to be applied to the sensors used in an ocean environment monitoring system, it is considered that there is a large possibility that the function of the sensors themselves deteriorates due to the conductive coating film or current flowing therethrough.

In the method in which seawater is electrolyzed in an electrolysis vessel to generate an antifouling substance included in seawater passing in the vicinity of an object to be protected, the antifouling substance is supplied into a complete open system so that it is dispersed by waves or tidal current. Hence, the antifouling substance must be produced continuously to maintain the concentration of the substance at a constant level in the vicinity of the object to be protected. In this case, a huge amount of electric power is consumed in the monitoring system. Also, there are problems that the equipment for electrolysis must be large, and the electrodes deteriorate due to damages or chemical erosion. Similar problems will arise even if electrodes are disposed in the vicinity of sensors without providing an electrolysis vessel. Moreover, in some items of measurement, data obtained by sensors contain significant errors if the antifouling substance exists around the sensors. Therefore, it is generally considered that the method should not be applied to sensors used for such measurements.

In an ocean environment monitoring system in which sensors are disposed to perform long term monitoring and they are located away from a structure or ship in the ocean, the overall size of the system and the amount of usable electrical power are limited. Accordingly, reduction of the size of the system, reduction of power consumption, and no maintenance work over a prolonged period of time are desired.

SUMMARY OF THE INVENTION

In view of the foregoing, it is an object of the present invention to provide an improved ocean environment monitoring system in which settlement of marine organisms onto sensors is prevented by an antifouling structure which can be operated by a reduced amount of electric power, substantially without causing environmental contamination in the hydrosphere and which produces little errors in measurements obtained by the sensors over a prolonged period of time.

Another object of the present invention is to provide an improved method for controlling the monitoring system as described above.

An ocean environment monitoring system according to a first aspect of the present invention has at least one sensor having a sensing portion disposed in a sensor chamber. The sensor chamber has an inlet port (first port) and an outlet port (second port) for seawater, and is provided with a pump for forcing seawater to flow inside the sensor chamber through the inlet port and outlet port, and electrodes for electrolyzing seawater to produce an antifouling substance in the seawater. A power supply unit is further provided for supplying the electrodes with current for the electrolysis of the seawater. The electrodes is provided preferably at the inlet port or at least in the vicinity of the inlet port of the sensor chamber in the present invention so that the antifouling substance produced at the electrodes is introduced into the sensor chamber and is dispersed therein.

It is preferable that a filter is provided at the inlet port of the sensor chamber so that at least a part of the filter serves as the electrodes, or so that the electrodes are arranged to supply an antifouling substance to the filter.

The sensor chamber may be immersed in its entirety in seawater during the operation thereof. Alternatively, the system may have a structure in which only the inlet port is positioned below the surface of seawater while the outlet port is positioned above the surface of the seawater. In this case, the inlet port of the sensor chamber may be positioned at an arbitrary depth in the sea by using a flexible inlet tube.

The monitoring system may be provided with a system controller for controlling the pump, the sensor and the power supply unit of the system in an interrelated manner.

The monitoring system may be provided with, additionally to the system controller, a densitometer for measuring concentration of the antifouling substance introduced in the sensor chamber, wherein the system controller has a function for synchronously activating and stopping the pump and the power supply for the electrodes to maintain the concentration of the antifouling substance within a predetermined range.

The system may be provided with a thermometer, additionally to the system controller, for detecting the temperature of seawater in the vicinity of the sensor chamber or inside the sensor chamber, wherein the system controller has a function for setting the range of concentration of the antifouling substance based on the output from the thermometer.

A switching device may be provided for the electrodes for coupling the positive and negative terminals of the power supply unit to the electrodes in different polarities.

The method for controlling the ocean environment monitoring system according to the first aspect of the present invention includes the steps of intermittently performing a measurement using at least one sensor, performing electrolysis of seawater using the electrodes each time after one of the measurements by the sensor is completed, introducing seawater containing an antifouling substance, which is generated by the electrolysis of the seawater, into the sensor chamber by the pump, stopping the power supply for the electrodes and driving the pump between the step of introducing the antifouling substance into the chamber and next one of the measurements so as to remove the antifouling substance from the chamber, and performing the next one of the measurements using the sensor after the removal of the antifouling substance in a state in which the pump is being driven or is stopped.

A step of stopping both the power supply and the pump, a step of activating both the power supply and the pump, or both the steps may be inserted between the step of introducing the antifouling substance into the chamber and the step of removing the antifouling substance.

Generally, when the concentration of an antifouling substance in the vicinity of an object to be protected exceeds a certain level (for example, 0.2 ppm), marine organisms avoid the object so that the settlement of marine organisms can be prevented. However, in seawater, the antifouling substance is generally dispersed by waves or tidal current and decomposed by other substances or sunlight to reduce the concentration of the substance. By employing the configuration of the present invention, in which the sensor is disposed in a sensor chamber and an antifouling substance provided in the vicinity of the inlet port of the sensor chamber is introduced into the sensor chamber, the dispersion and decomposition of the antifouling substance can be significantly decreased. Hence, by performing electrolysis in accordance with the degree of dispersion and decomposition, the power consumption, and damage and erosion of the electrodes can be reduced.

After the concentration of the antifouling substance is decreased due to the stop of power supply for the electrodes, marine organisms may be attached to the sensor. However, such marine organisms will leave the sensor after the antifouling substance is produced at the next time of the power supply for the electrodes. It is unnecessary to continuously maintain a high concentration of the antifouling substance. Therefore, an effect of preventing settlement of marine organisms can be obtained by intermittently performing electrolysis. This significantly reduces the power consumption, and the damage and erosion of the electrodes.

Especially, if a specific sensor is used which inherently generates an error due to the antifouling substance, the electrolysis by the electrodes is stopped before each of the measurements by the sensor and fresh seawater is introduced from outside the sensor chamber so as to lower the concentration of the antifouling substance during each of the measurements, thereby eliminating adverse effects on the measurement while effectively preventing marine biofouling.

By disposing a pair of electrodes in the vicinity of the seawater inlet port, settlement of marine organisms at the inlet port and outlet port for seawater can be prevented efficiently. When the inlet port and outlet port themselves are formed as electrodes, the settlement of marine organisms can be prevented more effectively. Since marine organisms floating around the inlet port and outlet port avoid the antifouling substance produced by electrolysis of seawater and electrical shock due to contact with the electrodes, the inlet and outlet ports are prevented from being blocked or clogged by marine organisms.

If filters are provided at the inlet port and outlet port of the sensor chamber, marine organisms larger than the mesh of the filters are blocked by the filters, so that the marine biofouling can be prevented more effectively by virtue of the filters together with the antifouling substance. By forming the electrodes in a configuration of a filter, the effect of electrical shock can be enhanced to thereby prevent blocking of the filter.

By performing electrolysis while supplying current depending on the water temperature and the quality of seawater, the power consumption for the electrolysis and damage and erosion of the electrodes can be decreased.

An ocean environment monitoring system according to a second aspect of the present invention has also at least one sensor having a sensing portion disposed in a sensor chamber. The sensor chamber has a first and a second ports thereof for introducing seawater inside the sensor chamber and for discharging seawater, and is provided with a pair of electrodes for electrolyzing seawater in the vicinity of each of the ports to produce an antifouling substance in seawater, a power supply unit for supplying the electrodes with current for the electrolysis, and a pump for forcing seawater to flow inside the sensor chamber, wherein the direction of flow of seawater is switched such that seawater flows from the first port to the second port or from the second port to the first port.

The monitoring system of the second aspect of the present invention may have a structure in which the sensor chamber has a configuration of V-character, the first and second ports are provided at the opposite ends of the V-character, and rotary vanes are provided at the sides of the corner of the sensor chamber, the rotary vanes serving as the pump for switching the direction of flow of seawater.

The pair of electrodes should be provided in the vicinity of at least one of the ports of the sensor chamber so that the antifouling substance produced at the electrodes is introduced into the sensor chamber and is dispersed therein.

A filter may be provided at least at one of the ports of the sensor chamber so that at least a part of the filter serves as the electrodes, or so that the electrodes are arranged to supply an antifouling substance to the filter.

The monitoring system of the second aspect may have a system controller for controlling the pump, the sensor, the power supply for the electrodes, and the direction of flow of seawater in an interrelated manner.

The system may be provided with a densitometer for measuring concentration of the antifouling substance introduced in the sensor chamber, wherein the system controller has a function for synchronously activating and stopping the pump and the power supply to maintain the concentration of the antifouling substance within a predetermined range.

The system may be provided with, additionally to the system controller, a thermometer for detecting the temperature of seawater in the vicinity of the sensor chamber or inside the sensor chamber, wherein the system controller has a function for setting the range of concentration of the antifouling substance based on the output from the thermometer.

The pair of electrodes may be provided with a switching device for coupling the positive and negative terminals of the power supply unit to the electrodes in different polarities.

The method for controlling the ocean environment monitoring system according to the second aspect of the present invention includes the steps of intermittently performing measurements by using at least one sensor, performing electrolysis of seawater using the electrodes each time after one of the measurements is completed, introducing seawater containing an antifouling substance generated by the electrolysis into the chamber by the pump, stopping the power supply for the electrodes and driving the pump between the step of introducing the antifouling substance and next one of the measurements so as to remove the antifouling substance from the chamber, and performing the next one of the measurements by using the sensor in a state in which the pump is being driven or is stopped, wherein the direction of flow of seawater flowing through the sensor chamber is changed in accordance with the amount of substances accumulated at the ports or filters or at a predetermined timing.

The step of stopping both the power supply for the electrodes and the pump, the step of activating both the power supply and the pump, or above the two steps may be inserted between the step of introducing the antifouling substance into the chamber and the step of removing the antifouling substance.

In general, in a sea area where a large amount of dirt floats in the seawater or mud stirs in the seawater, dirt and mud gradually accumulate on the filters and electrodes during operation over a prolonged period of time. However, these dirt and mud can be released into seawater in the second aspect of the present invention by the step in which the direction of flow of seawater is reversed. Due to little accumulation of dirt and mud, the amount of flow of seawater is maintained substantially constant any time. Since spores and larvae of marine organisms contained in dirt and mud hardly attach to the ports of the sensor chamber, the initial performance of preventing marine biofouling at the beginning of an operation can be maintained during the operation for a long period.

The above and other objects, features and advantages of the present invention will be more apparent from the following description, taken in conjunction with the accompanying drawings.

DESCRIPTION OF THE PREFERRED EMBODIMENTS

Now, embodiments of the present invention will be described with reference to the accompanying drawings.

First Embodiment

Figure 1:
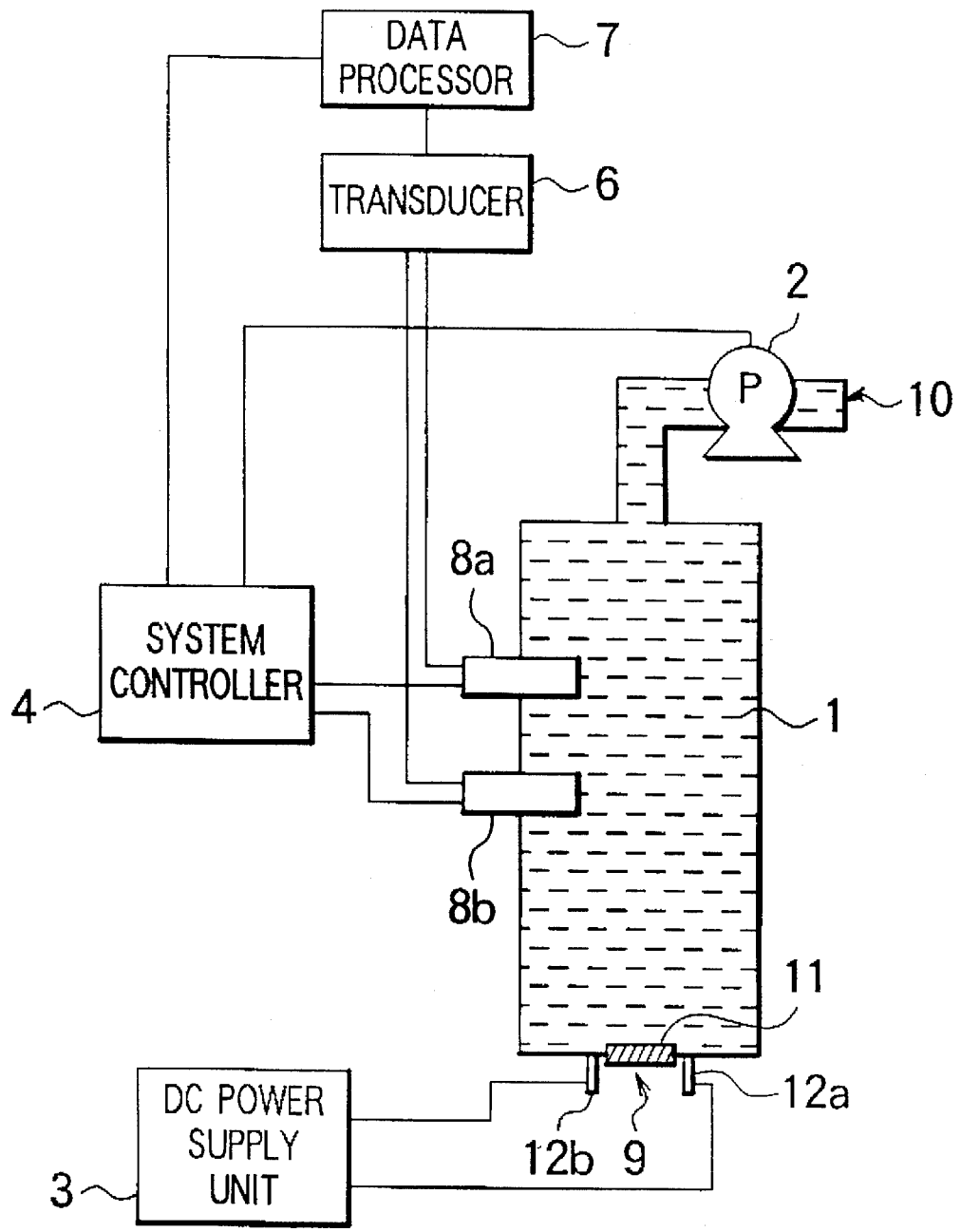
FIG. 1 is a block diagram showing a first embodiment of a monitoring system according to the present invention.

FIG. 1 shows an ocean environment monitoring system according to a first embodiment of the present invention. As shown in FIG. 1, the monitoring system is comprised of a plurality of sensors 8a and 8b, a sensor chamber 1, a pump 2, a DC power supply unit 3, a system controller 4, a transducer 6, and a data processor 7. The sensors 8a and 8b are disposed such that the sensing portions of the sensors 8a and 8b are located inside the sensor chamber 1. The data obtained by and output from the sensors 8a and 8b are transmitted to the data processor 7 via the transducer 6. The sensor chamber 1 has an inlet port 9 and an outlet port 10 for introducing and discharging seawater, respectively. Seawater can be introduced inside the sensor chamber 1 by the pump 2 disposed in the vicinity of the outlet port 10. A filter 11 is attached to the inlet port 9, and electrodes 12a and 12b are provided outside the sensor chamber 1 in the vicinity of the filter 11.

In operation, when the DC power supply unit 3 is turned on to supply current to the electrodes 12a and 12b, seawater is electrolyzed in the vicinity of the electrodes 12a and 12b to produce an antifouling substance such as chlorine and hypochlorous acid. When the pump 2 is driven in this state, the antifouling substance produced in the vicinity of the electrodes 12a and 12b is supplied onto the filter 11, inside the sensor chamber 1, and around the sensing portions of the sensors 8a and 8b located inside the sensor chamber 1, so as to prevent settlement of marine organisms onto those portions of the monitoring system. Substances larger than the mesh of the filter 11 are blocked by the filter 11. Owing to the function of the antifouling substance and the filter 11, the monitoring system can be continuously operated for a long period of time, so that highly reliable data can be obtained.

The antifouling substance exhibits an antifouling function at a concentration of the substance higher than a certain level, and the function is generally maintained for a relatively long period, for example, two hours. Hence, it is unnecessary to continuously operate the DC power supply unit 3 and the pump 2. Data for the relationship between the operation period of the DC power supply unit 3 as well as the pump 2 and the effect of preventing biofouling by the antifouling substance should be studied in advance for a specified monitoring system. Based on the data, the period for operating the DC power supply unit 3 and the pump 2 is predetermined to recover the function of the antifouling substance only when the effect of preventing biofouling is decreased. With this operation, the power consumption can be significantly reduced.

In some sensors, measurements are affected by existence of the antifouling substance, or measurements cannot be accurately performed if the amount of flow of seawater is too small. In case of such a sensor, measurement by the sensor should be intermittently performed. During the measurements, the DC power supply for the electrodes is stopped and the pump 2 is driven to produce a flow of fresh seawater passing inside the sensor chamber 1. During a period other than the measurement periods, the antifouling substance is generated by the electrodes and supplied into the sensor chamber 1 by the pump 2. While supply of the antifouling substance is stopped, marine organisms may be attached to the sensing portions of the sensors. However, such marine organisms will leave the sensing portions after the antifouling substance is supplied at the next time. Accordingly, substantially no problem will arise in such intermittent operation so long as the period for the stop of the supply of the antifouling substance is determined properly.

The activation and stop of the pump 2, the DC power supply unit 3 and the sensors 8 are controlled by the system controller 4.

The structure and the layout of the sensor chamber 1, the sensors 8, the pump 2, the electrodes 12 and the filter 11 may be modified so that satisfactory effects of preventing marine biofouling and satisfactory results of measurement can be obtained.

Figure 2A:
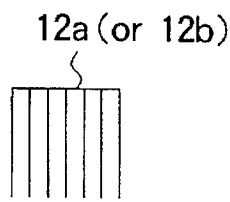
FIG. 2A and FIG. 2B are vertical views showing examples of the configuration of the electrode used in the present invention.
Figure 2B:
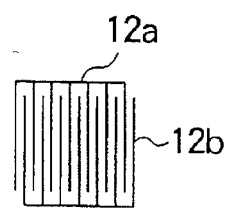
Figure 3:
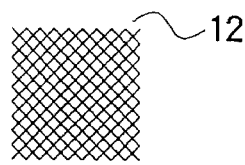
FIG. 3 and FIG. 4 are vertical views showing other examples of the configuration of the electrodes used in the present invention.
Figure 4:
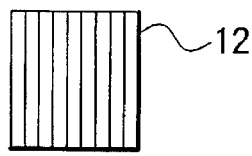

Although the electrodes 12a and 12b used in the first embodiment have a configuration of a plate, the electrodes 12a and 12b may be formed in a configuration of a comb as shown in FIG. 2A, and may be disposed on a common plane such that the teeth of one of the electrodes 12a and 12b does not touch the teeth of the other, as shown in FIG. 2B. Smaller distance between the electrodes 12a and 12b increases the efficiency of electrolysis and the effect of electric shock against marine organisms. The electrodes 12a and 12b may have a configuration of a mesh as shown in FIG. 3, or a grid as shown in FIG. 4. They are disposed opposite to each other to effect electrolysis of seawater to produce an antifouling substance.

Figure 5:
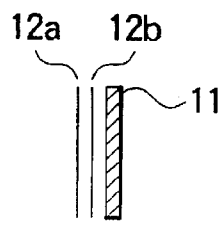
FIG. 5 through FIG. 7 are sectional views showing examples of the layout of the filter and the electrodes used in the present invention.
Figure 6:
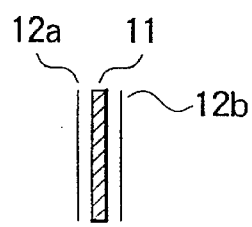
Figure 7:
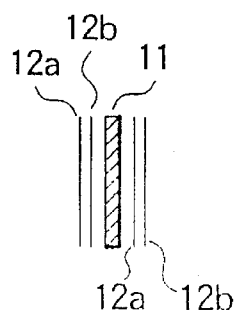

FIG. 5 through FIG. 7 show other examples of the layout of the filter 11 and the electrodes 12a and 12b. In FIG. 1, the electrodes 12a and 12b are disposed on the outer surface of the wall of the sensor chamber 1 to be located at the periphery of the filter 11. If the electrodes having the shape shown in FIGS. 2A, 3 and 4 are used, both the electrodes 12a and 12b may be disposed to entirely cover the outer side of the filter 11, as shown in FIG. 5. When the electrodes 12 are disposed parallel to the filter 11 to screen the same, the antifouling substance can be efficiently supplied to the filter 11. The structure shown in FIG. 6 may be also employed in which an insulator filter 11 is sandwiched between the electrodes 12a and 12b. A pair of electrodes 12a and 12b may be disposed adjacent to each side of the filter 11, as shown in FIG. 7.

Figure 8:
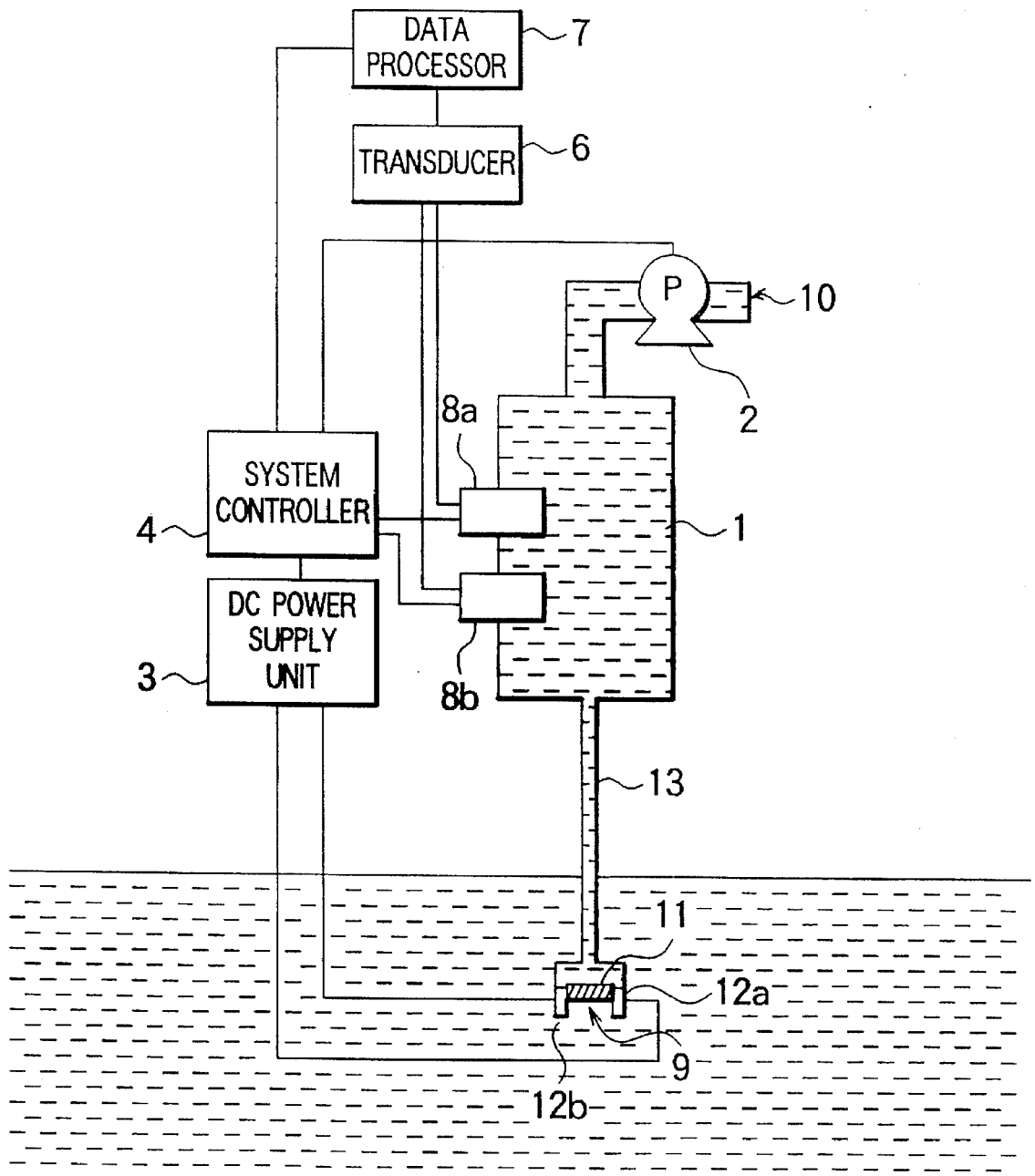
FIG. 8 is a block diagram showing a second embodiment of the monitoring system according to the present invention.

Second Embodiment:

FIG. 8 shows an ocean environment monitoring system according to a second embodiment of the present invention. As shown in FIG. 8, only an inlet port 9 for introducing seawater is immersed in seawater to be measured in contrast to the first embodiment in which both the ports are to be immersed in seawater. Seawater is pumped up through a tube 13 to a sensor chamber 1 in which the sensing portions of the sensors 8a and 8b are located. The sensors 8 can be installed above the surface of the sea accordingly to enable the maintenance thereof with ease. If the tube 13 is made of a flexible material, the depth of the inlet port 9 can be selected as desired, with the monitoring system be fixed as a whole. This makes it possible to measure the seawater at different depths.

The outlet port 10 may be positioned above the surface of the seawater, as shown in the drawing, or may be positioned in the seawater. The sensors 8a and 8b may be positioned such that a maintenance work for the sensors 8a and 8b is performed without pulling up the sensor chamber 1. Further, a structure may be employed such that it allows an operator to visually check the sensors 8a and 8b while they are installed for measuring, with the sensor chamber 1 being filled with seawater. When a maintenance work is to be performed for the filter 11 or the electrodes 12a and 12b, it is sufficient to pull up the filter 11 and the electrodes 12 together with the tube 13. Accordingly, the maintenance work can be easily performed even when the sensors 8a and 8b are large and heavy.

Figure 9:
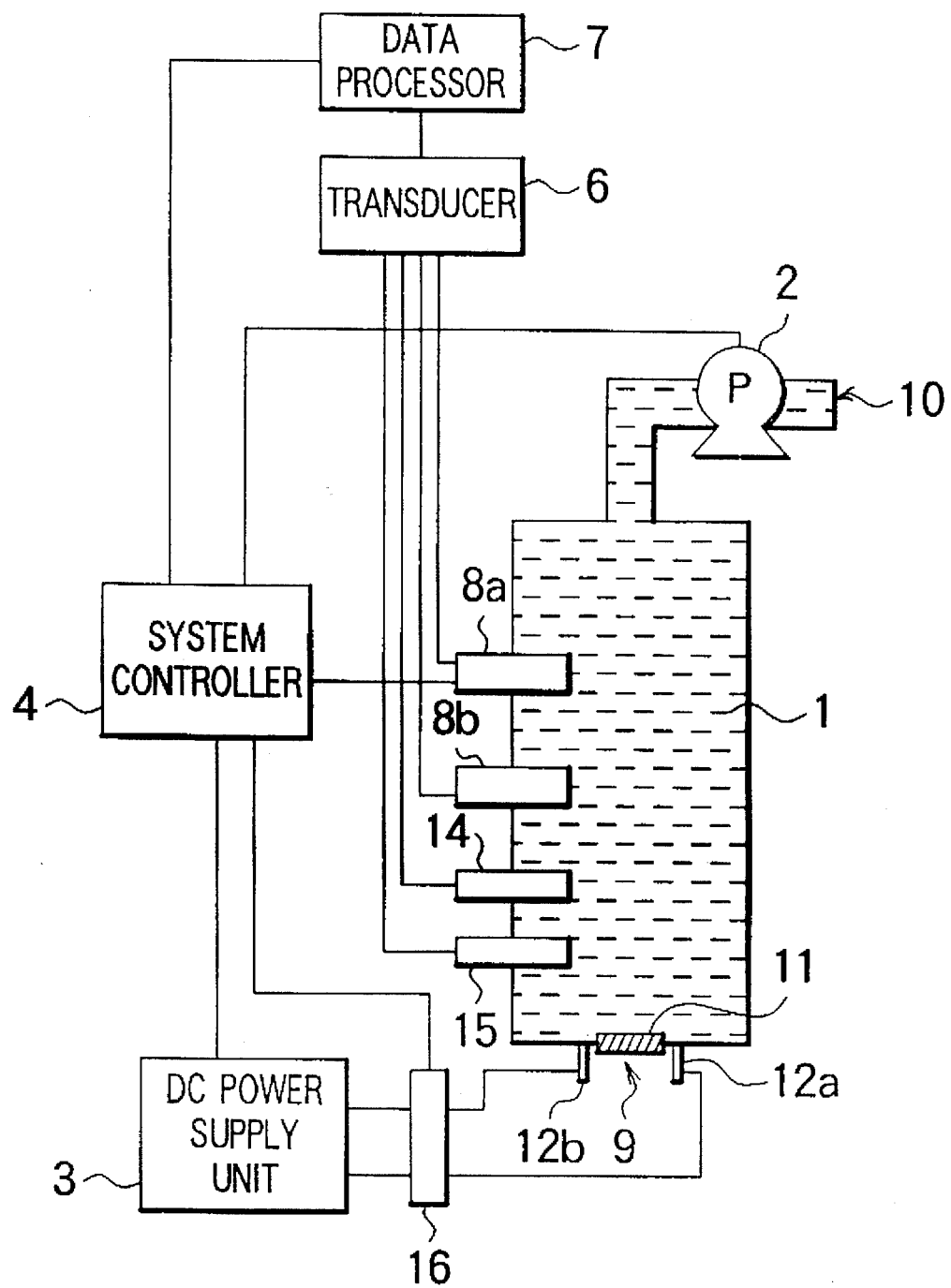
FIG. 9 is a block diagram showing a third embodiment of the monitoring system according to the present invention.

Third Embodiment:

FIG. 9 shows an ocean environment monitoring system according to a third embodiment of the present invention. In the present embodiment, a densitometer 14 for measuring the concentration of an antifouling substance, a thermometer 15 for measuring water temperature and a change-over switch 16 for changing the polarity of the voltage applied to the electrodes 12a and 12b are provided additionally to the system of the first embodiment shown in FIG. 1.

As described in relation to the first embodiment, it is sufficient that the concentration of the antifouling substance is maintained higher than a certain level. Based on the above configuration of the third embodiment, the power consumption can be significantly reduced by intermittently operating the DC power supply unit 3 and the pump 2, as will be described below. The system controller 4 in the present embodiment has a function for monitoring the concentration of the antifouling substance measured by the densitometer 14, and for controlling the activation and stop of the DC power supply unit 3 and the pump 2 for maintaining the concentration of the antifouling substance in a predetermined range. The current supplied from the power supply unit 3 to the electrodes 12a and 12b are also controlled by the system controller 4. With this function, marine biofouling can be effectively prevented while reducing the power consumption of the power unit 3 and the pump 2.

Generally, the activity of marine organisms is affected by the temperature of seawater, and settlement of the marine organisms is therefore affected by the water temperature. In the present embodiment, the system controller 4 selects a set value, which is used for controlling the concentration of the antifouling substance, based on the data obtained from the thermometer 15, and controls the DC power supply unit 3 and the pump 2 in accordance with the set value thus determined. With this function, marine biofouling can be prevented more effectively while obtaining a reduction of the power consumption.

In the present embodiment, the change-over switch 16 disposed between the electrodes 12a and 12b and the DC power supply 3 enables the electrodes 12a and 12b to act as any of a positive electrode and a negative electrode. If they are used for a long period without changing the polarities, magnesium hydroxide and calcium carbonate will be precipitated on the surface of the negative electrode, so that the performance of the electrode deteriorates. In the monitoring system according to the present embodiment, the polarities of the electrodes 12a and 12b are switched by change-over switch 16 at an interval of a few hours to reduce the precipitation of magnesium hydroxide and calcium carbonate.

Figure 10:
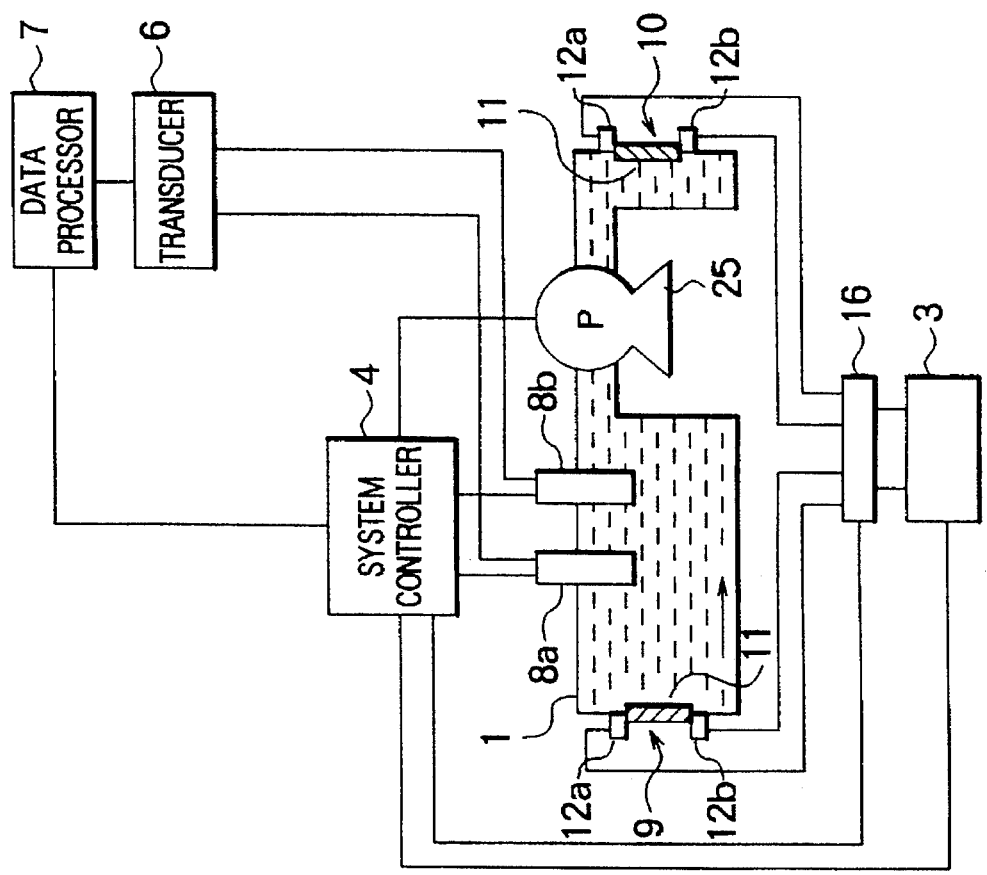
FIG. 10 is a block diagram showing a fourth embodiment of the monitoring system according to the present invention.

Fourth Embodiment:

FIG. 10 shows an ocean environment monitoring system according to a fourth embodiment of the present invention. As shown in FIG. 10, the monitoring system is comprised of a sensor chamber 1, a pump assembly 25, a DC power supply unit 3, a change-over switch 16, a system controller 4, a transducer 6, and a data processor 7. The pump assembly 25 is formed by combining two ordinary pumps such that the directions of suction and discharge of one of the pumps are opposite to those of the other. In this configuration, the direction of flow of seawater can be switched by selectively operating one of these pumps of the pump assembly 25.

The monitoring system according to the present embodiment has two sensors 8a and 8b which are disposed such that the sensing portions of the sensors 8a and 8b are located inside the sensor chamber 1. Measurement data obtained by the sensors 8a and 8b are transmitted to the data processor 7 via the transducer 6. The sensor chamber 1 has a first and a second ports 9 and 10 each provided with a filter 11. Seawater is forced to pass through inside the sensor chamber 1 in one of two opposite directions by the pump assembly 25. A pair of electrodes 12a and 12b are provided outside of each of the filters 11. Seawater can be electrolyzed at each of the pairs of electrodes 12a and 12b to produce an antifouling substance such as chlorine and hypochlorous acid which keeps off marine organisms.

The filters 11 provided in the vicinity of the ports 9 and 10 may be omitted. However, it is preferable that filters are used at both ports 9 and 10 of the sensor chamber 1 to block a larger substance. Due to the functions of the antifouling substance and the filters, settlement of marine organisms can be prevented more effectively. The electrodes may be formed in a configuration of a filter for generating an electric shock to block marine organisms from the sensor chamber more effectively. The sensor chamber 1 is immersed in seawater in its entirety during operation thereof.

When one of the pairs of the electrodes 12a and 12b is supplied with power, the antifouling substance is produced at the one of the pair of electrodes 12a and 12b. The antifouling substance is supplied to one of the filters 11, the sensor chamber 1 and the detecting portions of the sensors 8a and 8b. Substances larger than the mesh of the filters 11 are blocked by the filters 11. Due to the functions of the antifouling substance and the filters 11, the monitoring system can be continuously operated for a long period of time, so that highly reliable data can be obtained.

When the pump assembly 25 is operated to force seawater to flow in the direction indicated by an arrow, namely, from left to right, the antifouling substance produced at the electrodes 12a and 12b of the first port 9 is supplied to the interior of the sensor chamber 1 and to the detecting portions of the sensors 8a and 8b through the one of the filter 11. As a result, settlement of marine organisms onto the sensing portions of the sensors 8a and 8b can be reduced. The seawater is then discharged from the second port 10.

When the amount of dirt and mud accumulated in the vicinity of the first port 9 or second port 10 exceeds a predetermined level, or when a predetermined period of time elapses since the start of the operation of the pump assembly 25, the pump assembly 25 is switched to force seawater to flow in the direction opposite to the direction indicated by the arrow, namely, from right to left, and the antifouling substance produced at the electrodes 12a and 12b of the second port 10 is supplied to the interior of the sensor chamber 1 through the filter 11 of the second port 10.

In an under-water area where a large amount of dirt and mud floats and stirs, dirt and mud gradually accumulate at locations in the vicinity of the ports for introducing seawater, and on the electrodes and the filter. However, these accumulated dirt and mud can be removed at any time the direction of flow of seawater is reversed by the pump assembly 25. Accordingly, even in an under-water area where a large amount of dirt and mud exist, the amount of flow of seawater does not decrease in the present embodiment. Since spores and larvae of marine organisms contained in dirt and mud hardly attach to the ports of the sensor chamber, the effect of preventing marine biofouling continues for a long period.

The antifouling substance exhibits a biofouling effect at a concentration thereof higher than a certain level, and the effect is generally maintained for a certain period. Data for the relationship between the operation period of the DC power supply unit 3 and the pump 2 and the period for the antifouling effect should be studied in advance. Based on the data, the operation period for the DC power supply unit 3 and the pump 2 is determined to recover the effect only when the antifouling effect is decreased below a level corresponding to the certain level of the concentration. With this operation, the power consumption can be significantly reduced.

In some sensors, measurements are affected by existence of the antifouling substance, or measurements cannot be accurately performed if the amount of flow of seawater is too small. When such a sensor is used in the monitoring system according to the present embodiment, measurement by the sensor should be intermittently performed. During a measurement period, the DC power supply unit 3 is stopped and the pump assembly 25 is driven to provide a fresh seawater flowing inside the sensor chamber 1. During a period other than the measurement periods, the antifouling substance is supplied into the sensor chamber 1 by operation of the DC power supply unit 3 and by the pump assembly 25. When the supply of the antifouling substance is stopped, marine organisms may attached to the sensing portion of sensors. However, such marine organisms leave the portions to which they were attached when the antifouling substance is supplied at the next time. Accordingly, few problems will arise in such an intermittent operation. The direction of flow of seawater may be reversed when fresh seawater is to be passed through the sensor chamber 1.

The structure and the layout of the sensor chamber 1, the sensors 8, the pump assembly 25, the electrodes 12a and 12b, and the filters 11 may be modified so that a satisfactory antifouling effect and satisfactory results of measurement can be obtained.

In the present embodiment, the change-over switch disposed between the electrodes 12a and 12b and the DC power supply unit 3 enables the electrodes 12a and 12b to act as any of a positive electrode and a negative electrode. If they are used for a long period without changing the polarities, magnesium hydroxide and calcium carbonate will be precipitated on the surfaces of the negative electrodes so that the performance of the electrodes deteriorates. In the system according to the present embodiment, however, the polarities of the electrodes are switched by the change-over switch 16 at predetermined intervals to reduce the precipitation of magnesium hydroxide and calcium carbonate.

The activation and stop of the pump assembly 25, the DC power supply 3, the polarity switching device 15 and the sensors 8 are controlled by the system controller 4.

Figure 11:
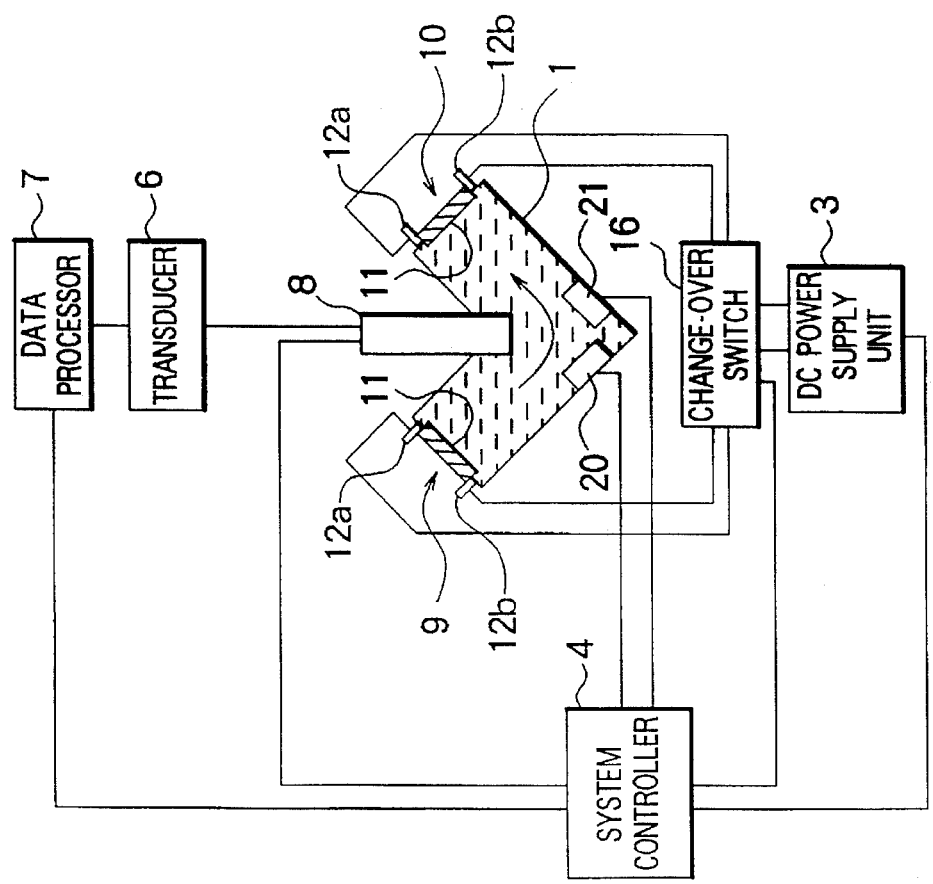
FIG. 11 is a block diagram showing a fifth embodiment of the monitoring system according to the present invention and FIG. 12 is a block diagram showing a sixth embodiment of the monitoring system according to the present invention.

Fifth Embodiment:

FIG. 11 shows an ocean environment monitoring system according to a fifth embodiment of the present invention. The present invention differs from the fourth embodiment shown in FIG. 10 in that the configuration of the sensor chamber 1 is modified in the present embodiment to have a configuration of a V-character. Ports 9 and 10 are provided at opposite ends of the V-shaped sensor chamber 1. Instead of the pump used in the fourth embodiment, two rotary vanes 20 and 21 are disposed on both sides of the bent corner of the sensor chamber 1. The rotary vanes 20 and 21 have a shape similar to vanes generally used in a magnetic pump. The monitoring system according to the present embodiment is operated by using one of the rotary vanes as a pump in a manner similar to the fourth embodiment. In operation, seawater flows in the direction indicated by an arrow when the vane 21 is driven, and flows in the direction opposite to the direction indicated by the arrow when the vane 20 is driven.

Figure 12:
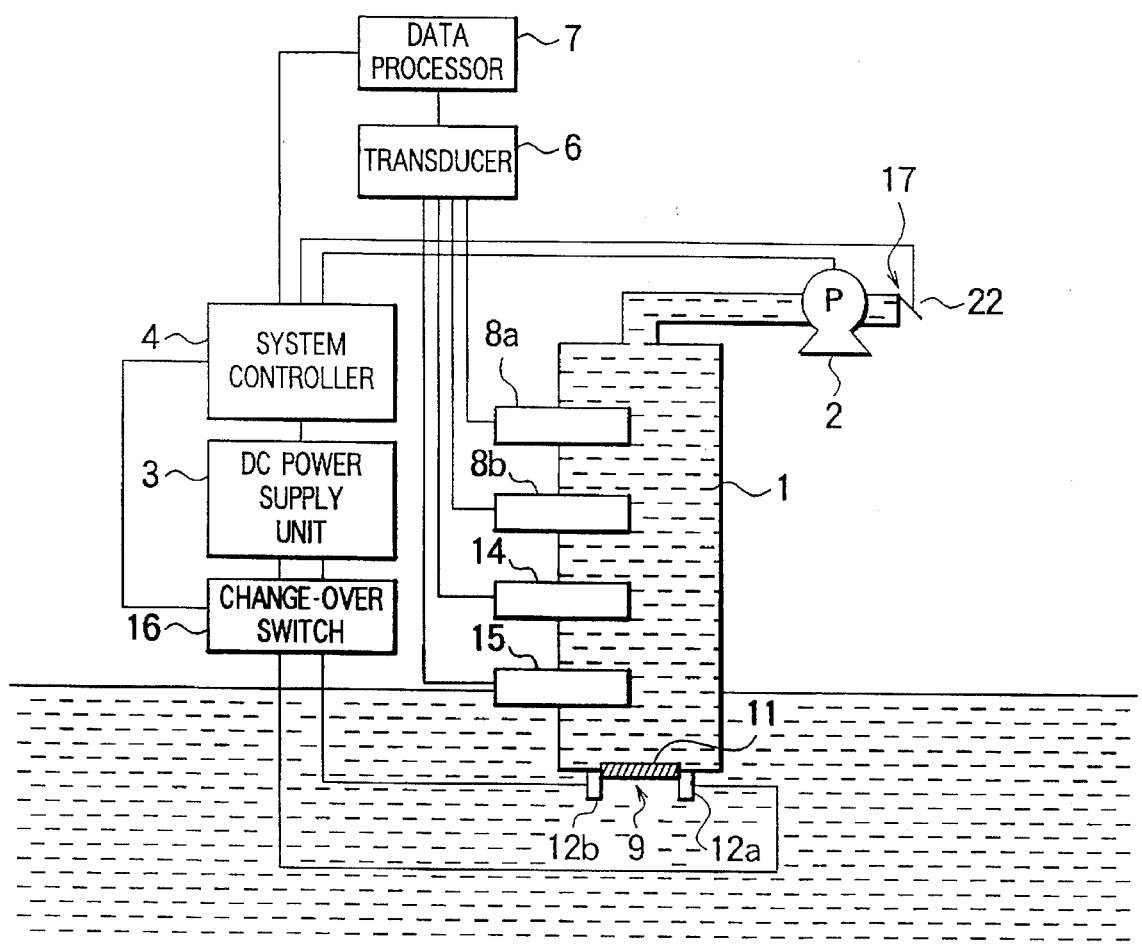

Sixth Embodiment:

FIG. 12 shows an ocean environment monitoring system according to a sixth embodiment of the present invention. In the present invention, a change-over switch 16 for electrodes, a valve 22 at the outlet port 17, a densitometer 14 for measuring the concentration of an antifouling substance, and a thermometer 15 are provided. The monitoring system is operated with the inlet port 11 immersed in seawater and with the outlet port positioned above the surface of seawater.

As described in relation to the fourth embodiment, dirt and mud accumulated on the filters and the electrodes can be removed by reversing the direction of flow of seawater. To reverse the direction of flow of seawater, a difference in height between a pair of ports is utilized.

The sensors 8a and 8b may be disposed above the surface of seawater or below the surface of seawater. In ordinary operation, the pump 2 operates such that fresh seawater which may or may not contain an antifouling substance is introduced from the inlet port 9 in seawater and discharged from the outlet port 17 disposed above the surface of seawater. The power consumption of the present embodiment can be reduced by intermittently operating the pump 2 as in the fourth embodiment.

In the present embodiment, the valve 22 provided at the outlet port 17 is closed to keep the seawater inside the sensor chamber 1 after the pump 2 is stopped. When the amount of dirt and mud accumulated in the vicinity of the inlet port 9 exceeds a predetermined level, or when a predetermined period of time elapses since the start of the operation of the pump 2, the valve 22 is opened simultaneously with or after the stop of the pump 2. With this operation, seawater flows out from the inlet port 9 so that dirt and mud accumulated at the locations in the vicinity of the inlet port 9 can be removed. The valve 22 is controlled by the system controller 4.

The system controller 4 in the present embodiment has a function for monitoring the concentration of the antifouling substance measured by the densitometer 14, and for controlling the activation and stop of the DC power supply unit 3 and the pump 2 for maintaining the concentration of the antifouling substance in a predetermined range. The current supplied from the power supply unit 3 to the electrodes are also controlled by the system controller 4. With this function, marine biofouling can be effectively prevented, and the power consumption can be significantly reduced.

The system controller 4 selects a set value, which is used for controlling the concentration of the antifouling substance, based on the data obtained from the thermometer 15, and controls the DC power supply unit 3 and the pump 2 in accordance with the set value thus determined. With this function, the prevention of biofouling, which is affected by the water temperature, and the reduction of the power consumption can be achieved more effectively.

Since above embodiments are described only for examples, the present invention is not limited to such embodiments and it will be obvious for those skilled in the art that various modifications or alterations can be easily made based on the above embodiments within the scope of the present invention.

What is claimed is:

1. An ocean environment monitoring system comprising: a sensor having a sensing portion thereof, a sensor chamber having a first and a second ports and receiving said sensing portion inside said sensor chamber, a pump for introducing seawater into said sensor chamber from said first port and discharging the seawater from said second port, a pair of electrodes, disposed in the vicinity of said first port, for electrolyzing the seawater to produce an antifouling substance included in seawater, and a power supply unit for applying between said pair of electrodes voltage for the electrolyzing.

2. An ocean environment monitoring system as defined in claim 1 wherein at least a part of said pair of electrodes implements a filter.

3. An ocean environment monitoring system as defined in claim 1 further comprising a filter disposed at said first port.

4. An ocean environment monitoring system as defined in claim 1 wherein said first port is disposed above said second port.

5. An ocean environment monitoring system as defined in claim 1 further comprising a system controller for controlling said sensor, said power supply unit and said pump.

6. An ocean environment monitoring system as defined in claim 5 further comprising a densitometer for measuring the concentration of said antifouling substance, wherein said system controller controls said power supply unit and said pump intermittently based on the output of said densitometer.

7. An ocean environment monitoring system as defined in claim 5 further comprising a thermometer for measuring temperature of the seawater, wherein said system controller controls said power supply unit and said pump based on the output of said thermometer.

8. An ocean environment monitoring system as defined in claim 1 further comprising a change-over switch for coupling said power supply unit and said pair of electrodes in different polarities.

9. An ocean environment monitoring system comprising: a sensor having a sensing portion thereof, a sensor chamber having a first and a second ports and receiving said sensing portion inside said sensor chamber, a pump assembly for introducing seawater into said sensor chamber from said first port and discharging the seawater from said second port, said pump assembly further capable of introducing seawater into said sensor chamber from said second port and discharging the seawater from said first port, a pair of electrodes, disposed in the vicinity of at least one of said first and second ports, for electrolyzing the seawater to produce an antifouling substance included in the seawater introduced into said sensor chamber, and a power supply unit for applying between said pair of electrodes voltage for the electrolyzing.

10. An ocean environment monitoring system as defined in claim 9 wherein said pump assembly is implemented by two pumps disposed in directions opposite to each other.

11. An ocean environment monitoring system as defined in claim 9 further comprising a filter disposed at each of said first and second ports.

12. An ocean environment monitoring system as defined in claim 11 wherein at least a part of said pair of electrodes implements said filter.

13. An ocean environment monitoring system as defined in claim 9 wherein said sensor chamber has a configuration of a V-character.

14. An ocean environment monitoring system as defined in claim 13 wherein said pump assembly is implemented by two rotary vanes for forcing seawater to flow in different directions.

15. An ocean environment monitoring system as defined in claim 9 further comprising a system controller for controlling said sensor, said power supply unit and said pump assembly.

16. An ocean environment monitoring system as defined in claim 15 further comprising a densitometer for measuring the concentration of said antifouling substance in the seawater, wherein said system controller controls said power supply unit and said pump assembly intermittently based on the output of said densitometer.

17. An ocean environment monitoring system as defined in claim 15 further comprising a thermometer for measuring temperature of the seawater, wherein said system controller controls said power supply unit and said pump based on the output of said thermometer.

18. An ocean environment monitoring system as defined in claim 9 further comprising a change-over switch for coupling said power supply unit and said pair of electrodes in different voltage polarities.

19. A method for operating an ocean environment monitoring system having a sensor, a sensor chamber receiving at least a sensing portion of the sensor, a pump for introducing seawater into the sensor chamber, and a pair of electrodes generating antifouling substance for the sensing portion, said method comprising the steps of: intermittently activating the sensor for measurements while stopping electrolyzing of seawater by the electrodes; introducing a antifouling substance by activating the electrodes for electrolyzing seawater and the pump for introducing the seawater into the sensor chamber after each one of the measurements; discharging the antifouling substance by stopping the activating of the electrodes while continuing the activating of the pump before a successive one of the measurements.

20. A method for operating an ocean environment monitoring system as defined in claim 19 further including the steps of stopping the activating of the electrodes and the pump before activating the sensor.

21. An ocean environment monitoring system as defined in claim 1, wherein the electrodes disposed in the vicinity of the first port enable the pump to introduce the seawater in the sensor chamber to provide a constant flow of the antifouling substance to the sensor inside the sensor chamber.

22. A method for operating an ocean environment monitoring system as defined in claim 19, wherein the electrodes disposed in the vicinity of the first port enable the pump to introduce the seawater in the sensor chamber to provide a constant flow of the antifouling substance to the sensor inside the sensor chamber.

* * * * *